(12) United States Patent
Birrer et al.

(10) Patent No.: US 10,296,769 B2
(45) Date of Patent: May 21, 2019

(54) METHOD FOR TEACHING POSITIONING OF A BAR CODE SCANNER AND APPARATUS FOR PROCESSING A SAMPLE OR REAGENT

(71) Applicant: Roche Molecular Systems, Inc., Pleasanton, CA (US)

(72) Inventors: Armin Birrer, Udligenswil (CH); Marco Sangermano, Kriens (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/420,300

(22) Filed: Jan. 31, 2017

(65) Prior Publication Data
US 2017/0220832 A1 Aug. 3, 2017

(30) Foreign Application Priority Data
Feb. 1, 2016 (EP) .................................... 16153650

(51) Int. Cl.
| G06K 7/10 | (2006.01) |
|---|---|
| G01N 35/00 | (2006.01) |
| G06K 7/14 | (2006.01) |
| G06K 19/06 | (2006.01) |

(52) U.S. Cl.
CPC ... *G06K 7/10603* (2013.01); *G01N 35/00732* (2013.01); *G06K 7/10544* (2013.01); *G06K 7/10861* (2013.01); *G06K 7/1452* (2013.01); *G06K 19/06028* (2013.01); *G01N 2035/00752* (2013.01)

(58) Field of Classification Search
CPC ................................................ G06K 7/10603
USPC ............ 235/462.08, 462.09, 462.11, 462.12, 235/462.14, 462.24, 454
See application file for complete search history.

(56) References Cited

U.S. PATENT DOCUMENTS

| 5,426,581 A | 6/1995 | Kishi et al. |
|---|---|---|
| 6,371,371 B1* | 4/2002 | Reichenbach ..... G06K 7/10851 235/454 |
| 6,672,511 B1* | 1/2004 | Shellhammer ....... G06K 9/3216 235/462.08 |
| 7,141,213 B1 | 11/2006 | Pang et al. |
| 8,371,505 B1* | 2/2013 | Zolotov ............. G06K 7/10722 235/462.24 |
| 2002/0020747 A1* | 2/2002 | Wakamiya ............... G06K 7/14 235/462.11 |
| 2003/0111536 A1 | 6/2003 | Mehlberg et al. |
| 2006/0108424 A1 | 5/2006 | Kim et al. |
| 2008/0035390 A1* | 2/2008 | Wurz ..................... G01B 11/04 177/25.15 |
| 2009/0095047 A1* | 4/2009 | Patel .................. G06K 7/10722 73/1.01 |

(Continued)

FOREIGN PATENT DOCUMENTS

EP 1496365 B1 6/2004

*Primary Examiner* — Allyson N Trail
(74) *Attorney, Agent, or Firm* — Pamela C. Ancona (57) ABSTRACT

A method for teaching positioning of a bar code scanner is disclosed. The method includes moving the bar code scanner relative to a first bar code so as to sweep a light beam emitted from the bar code scanner across the first bar code, detecting an orientation of the bar code scanner relative to the first bar code and positioning the bar code scanner based on the orientation. Further, an apparatus for processing a sample or reagent is disclosed.

11 Claims, 4 Drawing Sheets

(56) References Cited

U.S. PATENT DOCUMENTS

| | | |
|---|---|---|
| 2010/0288056 A1 | 11/2010 | Clark et al. |
| 2013/0065797 A1 | 3/2013 | Silbert et al. |
| 2015/0093290 A1* | 4/2015 | Takai ............... G01N 35/00732 422/65 |

* cited by examiner

METHOD FOR TEACHING POSITIONING OF A BAR CODE SCANNER AND APPARATUS FOR PROCESSING A SAMPLE OR REAGENT

CROSS REFERENCE TO RELATED APPLICATIONS

The present application claims the benefit of priority under 35 U.S.C. § 119 of EP16153650.3, filed Feb. 1, 2016, the content of which is incorporated herein by reference in its entirety.

FIELD OF THE INVENTION

The present invention relates to a method for teaching positioning of a bar code scanner and an apparatus for processing a sample or reagent using a bar code scanner.

RELATED ART

Bar code scanners are used in many technical fields. For example, bar code scanners are used to identify items bearing bar codes in an automated storage and retrieval system. In order to retrieve the correct item and to deliver it to the correct destination, the position of an accessor of the system should be carefully and accurately controlled. For this reason the bar code scanner is employed and the position of the bar code scanner must be accurately calibrated.

U.S. Pat. No. 5,426,581 A describes using a laser bar code scanner to calibrate positioning of a robotic system. The bar code scanner, which can also be used to read the identity of items stored in the system, is used to locate and scan each target and transmit to a controller a message containing the time during each sweep of the scanning beam when one side of the target is first detected and the time during each sweep when a second, opposing side, is detected. A processor calculates the physical center of the target based upon the transmitted times from one or more sweeps. The coordinates of the center are then stored and later used to accurately locate and retrieve an item stored in the system. The target is a fiducial that is rectangular and includes three rectangular light areas or marks on a dark background.

Bar code scanners may also be used with an apparatus for processing a sample or reagent for identification of consumables thereof. An apparatus for processing a sample or reagent as used herein can comprise a pipetting device for transferring a sample or reagent from a first vessel to a second vessel by means of an aspirating and dispensing operation. Modern apparatuses for processing samples of this kind are largely fully automatic in operation; only the samples stored in the vessels have to be inserted into the apparatus and the desired process such as an analysis is entered. Such apparatuses use different kinds of consumables. For identification purposes, the consumables can be provided with a bar code.

Bar code scanners are usually adjusted in order to read a bar code on a consumable at the correct position. For this purpose, an instrument head to which the bar code scanner is mounted has to be moved to a certain position where the scanner is mechanically adjusted in order to read at the right position.

While the use of the above-described apparatus for processing a sample or reagent provides advantages in terms of handling, there are still some drawbacks. While laser bar code scanners have a clearly visible reading position, cheaper non-laser bar code scanners only have an illumination in the reading optics that lightens a larger area than the position where the actual reading takes place. Thus, when using cheaper non-laser bar code scanners, it is difficult or even impossible to adjust the bar code scanner manually to a precise reading point as this point is not visible. Further, the bar code scanners need to scan bar codes on different items at different positions on these items. The bar code can be attached anywhere on a vertical side of these items. The bar code head is rather small such that the adjustment of the scanner on the instrument head is critical.

It is therefore an objective of the present invention to provide an improved method for teaching positioning of a bar code scanner and an apparatus for processing a sample or reagent using any kind of bar code scanner.

SUMMARY OF THE INVENTION

This problem is solved by a method for teaching positioning of a bar code scanner and an apparatus for processing a sample or reagent with the features of the independent claims. Embodiments of the invention, which may be realized in an isolated fashion or in any arbitrary combination, are listed in the dependent claims.

In one embodiment, the invention provides a method for teaching positioning of a bar code scanner, comprising
  moving the bar code scanner relative to a first bar code so as to sweep a light beam emitted from the bar code scanner across the first bar code,
  detecting an orientation of the bar code scanner relative to the first bar code, and
  positioning the bar code scanner based on the orientation, wherein the positioning step includes determining an offset of the bar code scanner from a target position and compensating for the offset.

Also provided is an apparatus for processing a sample or reagent, comprising
  a working surface provided with a first bar code,
  a moveable device comprising a bar code scanner mounted thereto such that the bar code scanner is moveable relative to the first bar code and configured to sweep a light beam emitted from the bar code scanner across the first bar code,
  at least one consumable provided with a third bar code, and
  a control device operably connected to the bar code scanner and adapted to compensate for an offset of the bar code scanner from a target position,
  wherein the apparatus detects an orientation of the bar code scanner relative to the first bar code, determines and compensates for the offset of the bar code scanner from the target position, and positions the bar code scanner.

BRIEF DESCRIPTION OF THE FIGURES

Further features and embodiments of the invention may be disclosed in more detail in the subsequent description of embodiments, preferably in conjunction with the dependent claims. Therein, the respective features may be realized in an isolated fashion as well as in any arbitrary feasible combination as the skilled person may realize. The embodiments are schematically depicted in the figures. Therein, identical reference numbers in these figures refer to identical elements or functionally identical elements.

DETAILED DESCRIPTION OF THE EMBODIMENTS

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the description that follows, in most cases, when referring to the respective feature or element, the expressions "at least one" or "one or more" will not be repeated, non-withstanding the fact that the respective feature or element may be present once or more than once.

The term "sample," as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having been mixed with reagents e.g. to carry out one or more diagnostic assays like e.g. clinical chemistry assays, immunoassays, coagulation assays, nucleic acid testing, etc. The term "sample" as used herein is therefore not only used for the original sample but also relates to a sample which has already been processed (pipetted, diluted, mixed with reagents, enriched, having been purified, having been amplified etc.). As used herein, the term "analyte" refers to the compound or composition to be detected or measured.

The term "reagent" is used to indicate a composition required for treatment of a sample. Reagents may be any liquid, e.g. a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g. to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, etc.

The term "processing a sample or reagent" may relate to transferring, aliquoting, isolating, purifying, incubating, treating or reacting a sample or reagent or combining a reagent with a sample.

It is to be noted that the terms "first," "second," "third" and "fourth" are exclusively used with the present invention to conceptually distinguish between the respective constructional members and are not intended to indicate any order of importance or the like.

According to the present invention, a method for teaching positioning of a bar code scanner is disclosed. The method comprises moving the bar code scanner relative to the first bar code so as to sweep a light beam emitted from the bar code scanner across the first bar code, detecting an orientation of the bar code scanner relative to the first bar code and positioning the bar code scanner based on the orientation.

Thus, the bar code scanner is moved relative to a first bar code while a light beam emitted from the bar code scanner sweeps across the first bar code. Thereby, the orientation of the bar code scanner relative to the first bar code may be detected as the bar code scanner reads the first bar code, the orientation and dimension thereof. By means of the thus detected orientation, the bar code scanner may be positioned. Therefore, the bar code scanner may be arranged in a fixed position relative to the device moving the bar code scanner. An offset may be detected at a first bar code and this offset is later used for all the different reading positions in the apparatus. By teaching or training the bar code scanner based on the position and offset of the first bar code, a more precise reading of the bar code by the bar code scanner is achieved that allows the scanner to differentiate between different bar codes in the apparatus which lie closer to each other. Unlike the method and apparatus described in U.S. Pat. No. 5,426,581, which uses specialty firmware that is not generally available in conventional bar code readers, the present method uses the code read-only function which is available on all types of off-the-shelf bar code scanners. Thus, all kinds of bar code scanners such as lasers, CCD, vision-based and the like can be used.

The first bar code may be stationary with respect to the bar code scanner. In other words, while the bar code scanner is moveable, the first bar code is fixed. Thus, for the teaching process, the first bar code is searched. As the first bar code is not moveable, any system tolerances between the bar code scanner and the first bar code are avoided and the relative orientation of the bar code scanner to the first bar code may be exactly detected.

The bar code scanner may be moved so as to sweep the light beam emitted from the bar code scanner across the first bar code at least within a first plane. Thus, an extension of the first bar code in a first direction may be detected.

The light beam may be swept within the first plane by means of a first reciprocal movement of the bar code scanner. Thus, an extension of the first bar code within this first plane may be detected.

The bar code scanner may be moved so as to sweep the light beam emitted from the bar code scanner across the first bar code within a second plane perpendicular to the first plane. Thus, a second extension of the first bar code in a second direction being perpendicular to the first direction may be detected.

The light beam may be swept within the second plane by means of a second reciprocal movement of the bar code scanner. Thus, a second dimension of the first bar code within this second plane may be detected.

The first bar code may comprise a first side and a second side. The second side is parallel and opposite to the first side. Detecting the orientation of the bar code scanner relative to the first bar code includes detecting the first side and the second side. Thus, the beginning and the end of the first bar code along a first axis may be detected.

The first bar code may comprise a third side and a fourth side, wherein the fourth side is parallel and opposite to the third side. Detecting the orientation of the bar code scanner includes detecting the third side and the fourth side. Thus, the beginning and the end of the first bar code along a second axis perpendicular to the first axis may be detected. This is particularly realized if the third side and the fourth side are perpendicular to the first side and the second side.

Positioning of the bar code scanner may include aligning the bar code scanner relative to the first bar code. Thus, the bar code scanner is adjusted relative to the first bar code.

Positioning of the bar code scanner may include determining an offset of the bar code scanner from a target position and compensating the offset. Thus, the offset may be later used for all different reading positions.

The orientation of the bar code scanner relative to a second bar code may be detected, wherein the second bar code is located in a different z-position compared to the first bar code. Thus, teaching of the bar code scanner along the z-axis is improved. This is particularly relevant in case bar codes and consumables are not arranged at the same position along the z-axis.

The bar code scanner may be mounted on a moveable device of an apparatus for processing a sample or reagent. The apparatus may comprise at least one consumable provided with a third bar code, wherein the consumable is identified by means of reading the third bar code by means of the bar code scanner. Thus, the consumable may be precisely identified.

The apparatus may comprise a working surface, wherein the first bar code may be provided to the working surface. Particularly, the first bar code may be mounted to the working surface. Thus, the first bar code is stationary and permanently arranged in the same position. Thus, the orientation of the bar code scanner relative to the first bar code may be precisely detected.

The moveable device may comprise moveable elements, wherein positioning of the bar code scanner may include aligning the bar code scanner relative to the first bar code by means of the moveable elements. Thus, the bar code scanner may be adjusted in its position.

The apparatus may comprise a control device, wherein positioning of the bar code scanner includes determining an offset of the bar code scanner from a target position and compensating the offset by means of the control device. Thus, an adjustment or fine tuning of the bar code scanner may be avoided. Rather, the control device takes into account any offset such as by means of calculating.

The moveable device may be at least one element selected from the group of: Pipetting device, gripping device, transporting device, rotating device, identifying device. The identifying device may be a bar code scanner attached to a robotic arm, a sensor, an RFID scanner or the like.

The consumable may be at least one element selected from the group consisting of: Pipetting tip, reagent vessel, sample vessel, reaction vessel, vessel carrier.

According to the present invention, an apparatus for processing a sample or reagent is disclosed. The apparatus comprises a working surface provided with the first bar code, a moveable device, a bar code scanner and at least one consumable provided with a third bar code. The bar code scanner is mounted to the moveable device. The bar code is moveable relative to the first barcode so as to sweep a light beam emitted from the bar code scanner across the first bar code. The apparatus is adapted to detect an orientation of the bar code scanner relative to the first bar code and to position the bar code scanner based on the orientation. Thus, the bar code scanner may be precisely orientated relative to any consumable used with the apparatus.

The first bar code may be mounted stationary with respect to the bar code scanner on the working surface. Thus, the first bar code serves as the fixed position for the teaching process.

The bar code scanner may be moveable so as to sweep the light beam emitted from the bar code scanner across the first bar code at least within the first plane.

The bar code scanner may be moveable such that the light beam is swept within the first plane by means of a first reciprocal movement of the bar code scanner.

The bar code scanner may be moveable so as to sweep the light beam emitted from the bar code scanner across the first bar code within a second plane perpendicular to the first plane.

The first bar code scanner may be moveable such that a light beam is swept within the second plane by means of a second reciprocal movement of the bar code scanner.

The first bar code may comprise a first side and a second side, wherein the second side is parallel and opposite to the first side, wherein the bar code scanner is adapted to detect the first side and the second side.

The first bar code may comprise a third side and a fourth side, wherein the fourth side is parallel and opposite to the third side, wherein the bar code scanner is adapted to detect the third and the fourth side.

The third side and the fourth side are perpendicular to the first side and the second side.

The bar code scanner may be alignable relative to the first bar code.

The apparatus may be adapted to determine an offset of the bar code scanner from a target position and to compensate the offset.

The apparatus may be adapted to identify the consumable by means of reading the third bar code by means of the bar code scanner.

The moveable device may comprise moveable elements, wherein the moveable elements are adapted to align the bar code scanner relative to the first bar code.

The moveable elements may be actuators.

The apparatus may further comprise a control device, wherein the control device is adapted to determine an offset of the bar code scanner from a target position and to compensate the offset by means of the control device.

The control device may comprise a computing device adapted to execute a software, wherein the software is adapted to compensate the offset by means of calculating.

The moveable device may be at least one element selected from the group of: Pipetting device, gripping device, transporting device, rotating device, identifying device.

The consumable may be at least one element selected from the group consisting of: Pipetting tip, reagent vessel, sample vessel, reaction vessel, vessel carrier.

The calculating may comprise calculating the mean value of the results in each plane following reciprocal movement of the bar code scanner.

The invention further discloses and proposes a computer program including computer-executable instructions for performing the method according to the present invention in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, preferably by using a computer program.

The invention further discloses and proposes a computer program product having program code means, in order to perform the method according to the present invention in one or more of the embodiments enclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present invention further discloses:
A computer or computer network comprising at least one processor, wherein the processor is adapted to perform the method according to one of the embodiments described in this description,
a computer loadable data structure that is adapted to perform the method according to one of the embodiments described in this description while the data structure is being executed on a computer,
a computer program, wherein the computer program is adapted to perform the method according to one of the embodiments described in this description while the program is being executed on a computer,
a computer program comprising program means for performing the method according to one of the embodiments described in this description while the computer program is being executed on a computer or on a computer network,
a computer program comprising program means according to the preceding embodiment, wherein the program means are stored on a storage medium readably to a computer,
a storage medium, wherein a data structure is stored on the storage medium and wherein the data structure is adapted to perform the method according to one of the embodiments described in this description after having been loaded into a main and/or working storage of a computer or of a computer network, and
a computer program product having program code means, wherein the program code means can be stored or are stored on a storage medium, for performing the method according to one of the embodiments described in this description, if the program code means are executed on a computer or on a computer network.

According, the following embodiments are disclosed:

Embodiment 1: a method for teaching positioning of a bar code scanner, comprising moving the bar code scanner relative to a first bar code so as to sweep a light beam emitted from the bar code scanner across the first bar code, detecting an orientation of the bar code scanner relative to the first bar code and positioning the bar code scanner based on the orientation.

Embodiment 2: a method according to the preceding embodiment, wherein the first bar code is stationary with respect to the bar code scanner.

Embodiment 3: a method according to any preceding embodiment, wherein the bar code scanner is moved so as to sweep the light beam emitted from the bar code scanner across the first bar code at least within a first plane.

Embodiment 4: a method according to the preceding embodiment, wherein the light beam is swept within the first plane by means of a first reciprocal movement of the bar code scanner.

Embodiment 5: a method according to any of the two preceding embodiments, wherein the bar code scanner is moved so as to sweep the light beam emitted from the bar code scanner across the first bar code within a second plane perpendicular to the first plane.

Embodiment 6: a method according to the preceding embodiment, wherein the light beam is swept within the second plane by means of a second reciprocal movement of the bar code scanner.

Embodiment 7: a method according to any preceding embodiment, wherein the first bar code comprises a first side and a second side, wherein the second side is parallel and opposite to the first side, wherein detecting the orientation of the bar code scanner includes detecting of the first side and the second side.

Embodiment 8: a method according to the preceding embodiment, wherein the first bar code comprises a third side and a fourth side, wherein the fourth side is parallel and opposite to the third side, wherein the orientation of the bar code scanner includes detecting of the third side and the fourth side.

Embodiment 9: a method according to the preceding embodiment, wherein the third side and the fourth side are perpendicular to the first side and the second side.

Embodiment 10: a method according to any preceding embodiment, wherein positioning of the bar code scanner includes aligning of the bar code scanner relative to the first bar code.

Embodiment 11: a method according to any preceding embodiment, wherein positioning of the bar code scanner includes determining an offset of the bar code scanner from a target position and compensating the offset.

Embodiment 12: a method according to any of the preceding embodiments, wherein the orientation of the bar code scanner relative to a second bar code is detected, wherein said second bar code is located in a different z-position, compared to said first bar code.

Embodiment 13: a method according to any preceding embodiment, wherein the bar code scanner is mounted on a moveable device of an apparatus for processing a sample or reagent, wherein the apparatus comprises at least one consumable provided with a third bar code, wherein the consumable is identified by means of reading the third bar code by means of the bar code scanner.

Embodiment 14: a method according to the preceding embodiment, wherein the apparatus comprises a working surface, wherein the first bar code is provided to the working surface.

Embodiment 15: a method according to any of the two preceding embodiments, wherein the moveable device comprises moveable elements, wherein positioning of the bar code scanner includes aligning of the bar code scanner relative to the first bar code by means of the moveable elements.

Embodiment 16: a method according to any of the three preceding embodiments, wherein positioning of the bar code scanner includes determining an offset of the bar code scanner from a target position and compensating the offset by means of a control device.

Embodiment 16A: a method according to any of the preceding embodiments, wherein said apparatus comprises a control device.

Embodiment 17: a method according to any of the four preceding embodiments, wherein the moveable device is at least one element selected from the group of: pipetting device, gripping device, transporting device, rotating device, identifying device.

Embodiment 18: a method according to any of the five preceding embodiments, wherein the consumable is at least one element selected from the group consisting of: pipetting tip, reagent vessel, sample vessel, reaction vessel, vessel carrier.

Embodiment 19 an apparatus for processing a sample or reagent, comprising a working surface provided with a first bar code, a moveable device, a bar code scanner, and at least one consumable provided with a third bar code, wherein the bar code scanner is mounted to the moveable device, the bar code scanner is moveable relative to the first bar code so as to sweep a light beam emitted from the bar code scanner across the first bar code, wherein the apparatus is adapted to detect an orientation of the bar code scanner relative to the first bar code and to position the bar code scanner based on the orientation.

Embodiment 20: an apparatus according to the preceding embodiment, wherein the first bar code is mounted stationary with respect to the bar code scanner on the working surface.

Embodiment 21: an apparatus according to any preceding embodiment, wherein the bar code scanner is moveable so as to sweep the light beam emitted from the bar code scanner across the first bar code at least within a first plane.

Embodiment 22: an apparatus according to the preceding embodiment, wherein the bar code scanner is moveable such that the light beam is swept within the first plane by means of a first reciprocal movement of the bar code scanner.

Embodiment 23: an apparatus according to any of the two preceding embodiments, wherein the bar code scanner is moveable so as to sweep the light beam emitted from the bar code scanner across the first bar code within a second plane perpendicular to the first plane.

Embodiment 24: an apparatus according to the preceding embodiment, wherein the bar code scanner is moveable such that the light beam is swept within the second plane by means of a second reciprocal movement of the bar code scanner.

Embodiment 25: an apparatus according to any preceding embodiment, wherein the first bar code comprises a first side and a second side, wherein the second side is parallel and opposite to the first side, wherein the bar code scanner is adapted to detect the first side and the second side.

Embodiment 26: an apparatus according to the preceding embodiment, wherein the first bar code comprises a third side and a fourth side, wherein the fourth side is parallel and opposite to the third side, wherein the bar code scanner is adapted to detect the third side and the fourth side.

Embodiment 27: an apparatus according to the preceding embodiment, wherein the third side and the fourth side are perpendicular to the first side and the second side.

Embodiment 28: an apparatus according to any preceding embodiment, wherein the bar code scanner is alignable relative to the first bar code.

Embodiment 29: an apparatus according to any preceding embodiment, wherein the apparatus is adapted to determine an offset of the bar code scanner from a target positoin and to compensate the offset.

Embodiment 30: an apparatus according to any preceding embodiment, wherein the apparatus is adapted to identify the consumable by means of reading the third bar code by means of the bar code scanner.

Embodiment 31: an apparatus according to the preceding embodiment, wherein the moveable device comprises moveable elements, wherein the moveable elements are adapted to align the bar code scanner relative to the first bar code.

Embodiment 32: an apparatus according to the preceding embodiment, wherein the moveable elements are actuators.

Embodiment 33: an apparatus according to any of the three preceding embodiments, further comprising a control device, wherein the control device is adapted to determine an offset of the bar code scanner from a target position and to compensate the offset by means of the control device.

Embodiment 34: an apparatus according to the preceding embodiment, wherein the control device comprises a computing device adapted to execute a software, wherein the software is adapted to compensate the offset by means of calculating.

Embodiment 35: an apparatus according to any of the five preceding embodiments, wherein the moveable device is at least one element selected from the group of: pipetting device, gripping device, transporting device, rotating device.

Embodiment 36: an apparatus according to any of the five preceding embodiments, wherein the consumable is at least one element selected from the group consisting of: pipetting tip, reagent vessel, sample vessel, reaction vessel, vessel carrier.

Embodiment 37: an apparatus according to embodiment 34, wherein the calculating comprises calculating the mean value of the results in each plane following reciprocal movement of the bar code scanner.

Figure 1:
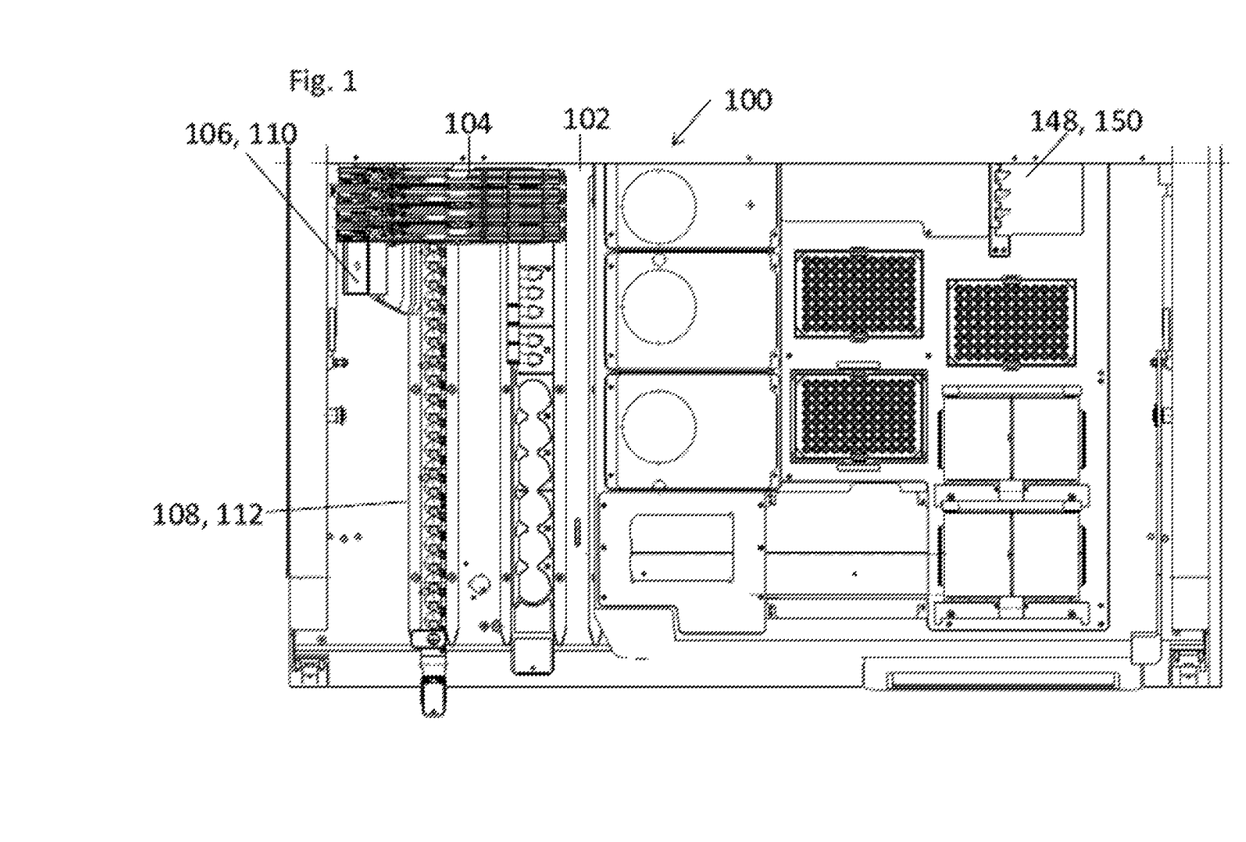
FIG. 1 shows a plan view of an apparatus for processing a sample or reagent.

FIG. 1 shows a plane view of an apparatus 100 for processing a sample or reagent according to the present invention. The apparatus comprises a working surface 102, a moveable device 104, a bar code scanner 106 and at least one consumable 108. The moveable device 104 may be at least one element or device selected from the group consisting of: Pipetting device, gripping device, transporting device, rotating device. In the exemplary embodiment shown in FIG. 1, the moveable device 104 is a pipetting device 160 combined with an identifying device 110. The consumable 108 may be at least one element selected from the group consisting of: Pipetting tip, reagent vessel, sample vessel, reaction vessel, vessel carrier. In the present embodiment, the consumable 108 is a vessel carrier 112.

Figure 2A:
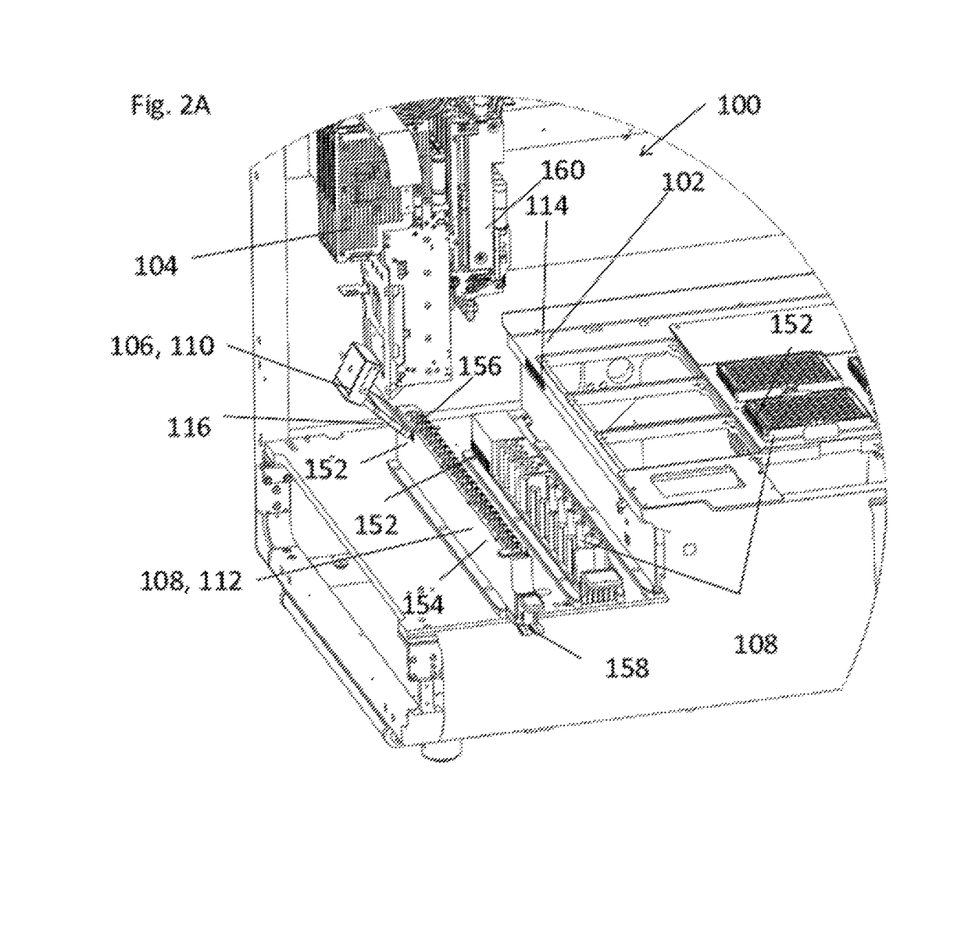
FIG. 2A shows a perspective view of the apparatus.
Figure 2B:
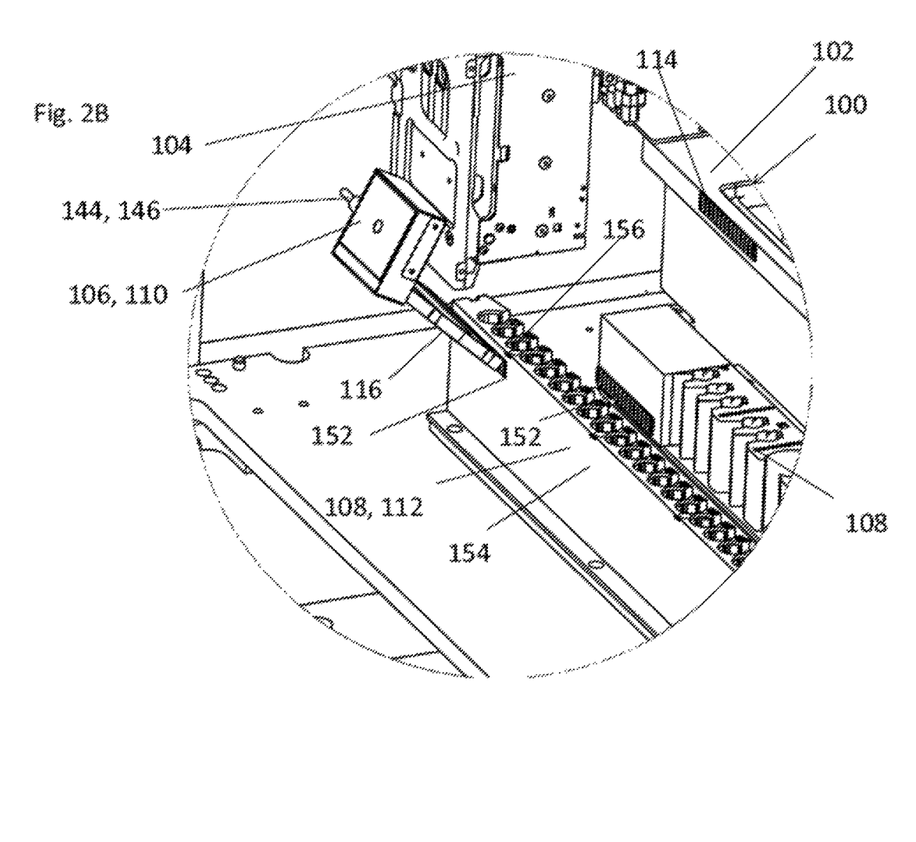
FIG. 2B shows an enlarged view of a part of FIG. 2A.

FIG. 2A shows a perspective view of the apparatus 100. FIG. 2B shows an enlarged view of a part of FIG. 2A. The working surface 102 is provided with a first bar code 114. For example, the first bar code 114 is mounted stationary on the working surface 102. The bar code scanner 106 is mounted to the moveable device 104. Thus, the first bar code 114 is stationary with respect to the bar code scanner 106.

Figures 3A, 3B:
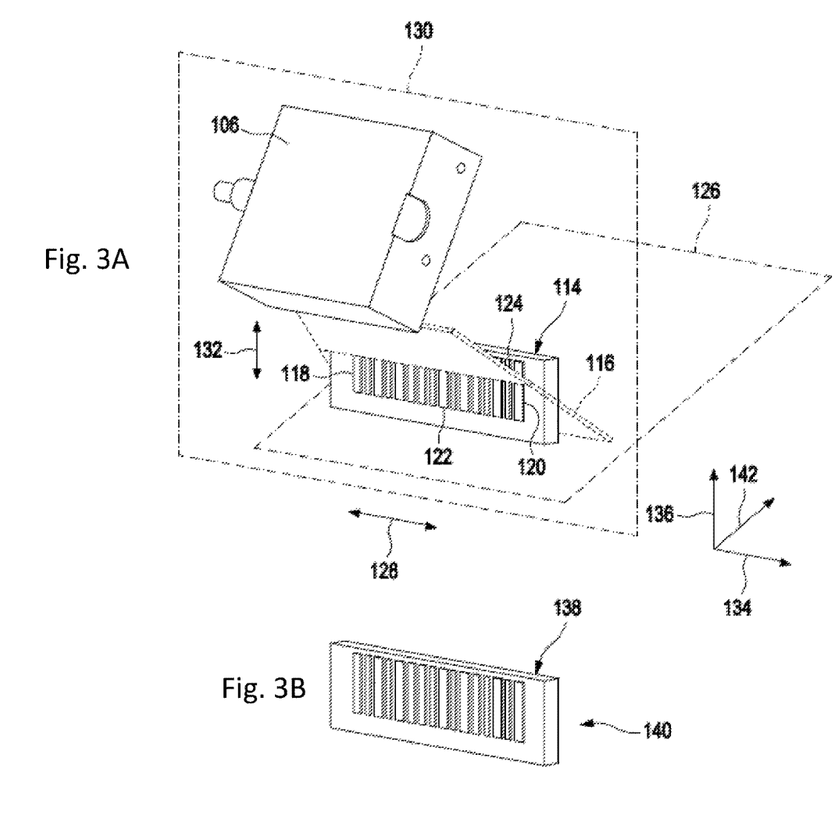
FIG. 3A shows an enlarged view of a bar code scanner.
FIG. 3B shows an enlarged view of a bar code.

FIG. 3 shows an enlarged view of the bar code scanner 106. By means of the moveable device 104, the bar code scanner 106 is moveable relative to the first bar code 114. The bar code scanner 106 is configured to emit a light beam 116. Particularly, the bar code scanner 106 is moveable relative to the first bar code 114 to sweep the light beam 116 emitted from the bar code scanner 106 across the first bar code 114. The apparatus 100 is adapted to detect an orientation of the bar code scanner 106 relative to the first bar code 114 and to position the bar code scanner 106 based on the orientation as will be explained in further detail below.

As shown in FIG. 3, the first bar code 114 comprises a first side 118, a second side 120, a third side 122 and a fourth side 124. The respective sides 118, 120, 122 and 124 of the first bar code 114 represent the outer limits of the first bar code 114. The second side 120 is parallel and opposite to the first side 118. The fourth side 124 is parallel and opposite to the third side 122. The third side 122 and the fourth side 124 are perpendicular to the first side 118 and the second side 120. Thus, considering the outer limits of the first bar codes, the sides 118, 120, 122, 124 basically represent a rectangular shape.

Herein after, a method for teaching positioning of the bar code scanner 106 which may be used with the apparatus 100 will be explained. The bar code scanner 106 is moved so as to sweep the light beam 116 emitted from the bar code scanner 106 across the first bar code at least within a first plane 1126. The first plane 126 is parallel to the third side 122 and the fourth side 124. The light beam 116 is swept within the first plane 126 by means of a first reciprocal movement 128 of the bar code scanner 106. Further, the bar code scanner 106 is moved so as to sweep the light beam 116 emitted from the bar code scanner 106 across the first bar code 114 within a second plane 130 which is perpendicular to the first plane 126. The light beam 116 is swept within the second plane 130 by means of a second reciprocal movement 132 of the bar code scanner 106. An orientation of the bar code scanner 106 is detected relative to the first bar code 114. Particularly, the orientation detection includes detecting of the first side 118, the second side 120, the third side 122 and the fourth side 124 by means of the above described reciprocal movements 128, 132. Thus, the orientation of the bar code scanner 106 is detected along a y-axis 134 and along a z-axis 136 perpendicular to the y-axis 134.

In order to improve the teaching process, optionally the orientation of the bar code scanner 106 may be detected relative to a second bar code 138. The second bar code 138 is located in a different z-position 140 compared to the first bar code 114. In other words, the second bar code 138 is located at a different position 140 of the z-axis 36 perpendicular to the y-axis 134 and a x-axis 142. Based on the orientation, the bar code scanner 106 is positioned. Needless to say, the bar code scanner 106 is also moveable along the x-axis 142. It is to be noted that the first plane 126 is defined by the y-axis 134 and the x-axis 142, whereas the second plane 130 is defined by the y-axis 134 and the z-axis 136. The positioning of the bar code scanner 106 includes aligning the bar code scanner 106 relative to the first bar code 114. For this purpose, the moveable device 104 comprises moveable elements 144 by means of which the bar code scanner 106 may be positioned relative to the first bar code 114. The moveable elements 144 may be actuators 146 mounted to the moveable device 104.

Further, positioning of the bar code scanner 106 includes determining an offset of the bar code scanner 106 from a target position and compensating the offset. For this purpose, the apparatus 100 comprises a control device 148. By means of the control device 148, the offset may be compensated. The control device 148 comprises a computing device 150. The computing device 150 is adapted to execute a software program. The software is adapted to compensate the offset by means of calculating. The calculating process comprises calculating the mean value of the results in each plane 126, 130, following the reciprocal movements 128, 132 of the bar code scanner 106. In other words, the software calculates a first mean value from the first side 118 and the second side 120 and determines a first correct positioning to be in the middle therebetween. Similarly, the software calculates a second mean value from the third side 122 and the fourth side 124 and determines a second correct positioning to be in the middle therebetween.

If the bar code scanner 106 and the positioning thereof are taught, the bar code scanner 106 is ready to be used. For example, the consumable 108 is provided with a third bar code 152. The third bar code 152 may be adhered to a lateral or vertical surface 154 of the consumable 108. The apparatus 100 identifies the consumable 108 by means of reading the third bar code 152 by means of the bar code scanner 106. Since such a reading process of a bar code scanner 106 is well-known to the person skilled in the art, a detailed description of the reading process is omitted. Thereby, the vessel carrier 112 may be identified. For example, the vessel carrier 112 carries at least one vessel 156. The vessel 156 may be transported to a target position by means of a transporting device 158 where a pipetting device 160 of the apparatus 100 processes a sample stored in the vessel 156. Needless to say, further consumables 108 may be provided, wherein each of the consumables bears a bar code such as one of the type of the third bar code 152.

LIST OF REFERENCE NUMBERS

100 Apparatus
102 Working surface
104 Moveable device
106 Bar code scanner
108 Consumable
110 Identifying device
112 Vessel carrier
114 First bar code
116 Light beam
118 First side
120 Second side
122 Third side
124 Fourth side
126 First plane
128 First reciprocal movement
130 Second plane
132 Second reciprocal movement
134 y-axis 136 z-axis
138 Second bar code
140 z-position
142 x-axis
144 Moveable elements
146 Actuator
148 Control device
150 Computing device
152 Third bar code
154 Vertical surface
156 Vessel
158 Transporting device
160 Pipetting device

* * *

All patents, patent applications, publications, and descriptions mentioned herein are incorporated by reference in their entirety for all purposes. None is admitted to be prior art.

The invention claimed is:

1. A method for teaching positioning of a movable bar code scanner, comprising
moving the bar code scanner relative to a first bar code so as to sweep a light beam emitted from the bar code scanner across the first bar code, wherein the first bar code is stationary relative to the bar code reader,
detecting an orientation of the bar code scanner relative to the first bar code, and
positioning the bar code scanner based on the orientation, wherein the positioning step includes determining an offset of the bar code scanner from a target position by calculating a mean value of a bar code position in each plane following reciprocal movement of the bar code scanner and compensating for the offset.

2. A method according to claim 1, wherein the bar code scanner is moved so as to sweep the light beam emitted from the bar code scanner across the first bar code at least within a first plane.

3. A method according to claim 1, wherein the first bar code comprises a first side and a second side, wherein the second side is parallel and opposite to the first side, wherein the detecting step includes detecting the first side and the second side.

4. A method according to claim 1, wherein the orientation of the bar code scanner relative to a second bar code is detected, wherein the second bar code is stationary relative to the bar code scanner, wherein the first bar code is located in a first z-position and the second bar code is located in a second z-position, and the first and second z-positions are different.

5. A method according to claim 1, wherein the bar code scanner is mounted on a moveable device of an apparatus for processing a sample or reagent, wherein the apparatus comprises at least one consumable provided with a third bar code, wherein the consumable is identified by reading the third bar code using the bar code scanner.

6. A method according to claim 1, wherein the moveable device comprises at least one of the following elements: a pipetting device, gripping device, transporting device, rotating device, or an identifying device.

7. A method according to claim 5, wherein the consumable comprises at least one of the following elements: pipetting tip(s), a reagent vessel, a sample vessel, a reaction vessel, or a vessel carrier.

8. An apparatus for processing a sample or reagent, comprising
a working surface provided with a first bar code, wherein the first bar code is stationary within the apparatus,
a moveable device comprising a bar code scanner mounted thereto such that the bar code scanner is moveable relative to the first bar code and configured to sweep a light beam emitted from the bar code scanner across the first bar code,
at least one consumable provided with a third bar code, wherein the third bar code is stationary within the apparatus, and
a control device operably connected to the bar code scanner, wherein the control device comprises a computing device adapted to execute a software program configured to compensate for an offset of the bar code scanner from a target position by calculating a mean value of a bar code position in each plane following reciprocal movement of the bar code scanner,
wherein the apparatus detects an orientation of the bar code scanner relative to the first bar code, determines and compensates for the offset of the bar code scanner from the target position, and positions the bar code scanner.

9. An apparatus according to claim 8, wherein the bar code scanner is moveable so as to sweep the light beam emitted from the bar code scanner across the first bar code at least within a first plane.

10. An apparatus according to claim 8, wherein the first bar code comprises a first side and a second side, wherein the second side is parallel and opposite to the first side, wherein the bar code scanner is adapted to detect the first side and the second side.

11. An apparatus according to claim 8, wherein the moveable device comprises one of more of the following elements: a pipetting device, a gripping device, a transporting device, and a rotating device.

* * * * *